ROSE PLANT

Filed Jan. 18, 1971 2 Sheets-Sheet 1

MARIA MOLINA

By
Burns, Doane, Swecker & Mathis
Attorneys

ROSE PLANT

Filed Jan. 18, 1971 2 Sheets-Sheet 2

United States Patent Office

Plant Pat. 3,321
Patented May 1, 1973

3,321

ROSE PLANT

Maria Molina, Santa Ana, Calif., assignor to Clarence Amling Roses, Inc., Santa Ana, Calif.

Filed Jan. 18, 1971, Ser. No. 107,599
Int. Cl. A01h 5/00
U.S. Cl. Plt.—20 1 Claim

ABSTRACT OF THE DISCLOSURE

A rose plant of the hybrid tea class, discovered as a sport of the rose Baccara (Plant Patent No. 1,367) but of distinct red color, and is less affected by weather conditions, with more abundant flowers produced on strong growth.

SUMMARY OF THE INVENTION

This invention relates to a new and distinct variety of rose plant of the hybrid tea class which was discovered by me as a cultivated bud sport of the variety known as Baccara (U.S. Plant Patent No. 1,367).

This new rose was discovered by me in the course of my work grading commercially grown cut flowers of Baccara in a greenhouse located in Santa Ana, Calif. In the course of examining and grading the flowers cut from the variety known as Baccara my attention was attracted to one particular flower which was of better form and of a more red color than the rest.

Upon close examination of this flower, I noted that it was markedly distinct from all other flowers of Baccara and I therefore took steps to preserve this sport and have it asexually reproduced. Observation of the growth characteristics and bloom of new plants grown from those asexually reproduced confirmed new and distinctive characteristics of the flower color and form of the sport and conclusively established the transmission of these characteristics through succeeding asexual propagation.

My new rose is distinct from its parent by being of different flower color in all stages from calyx break through the useful life of the flower. This distinctive color difference is apparent on the inner petal surface and the outer petal surface and on all petals. In general color terms, the color is a deeper red with less yellow in its overall color effect. The bud form and shape are more uniform in my sport than in the parent, giving a higher yield of good quality flowers. The color and flower form of my sport are more uniform through all seasons of the year and through different weather and light conditions than the parent under the same adverse conditions. My sport has fewer petals than its parent with a resulting vase life, when cut, averaging one day less than its parent. The plants of my new rose are substantially the same as Baccara except for a tendency to make stronger growth and to make branches more freely which in turn will give more blooms per plant, and the foliage is somewhat less glossy than its parent.

BRIEF DESCRIPTION OF DRAWING

The accompanying drawings show typical specimens of my new variety in different stages of development, and as depicted in color as nearly true as it is reasonably possible to make the same in a color illustration of this character, wherein.

DETAILED DESCRIPTION OF DISCLOSURE

Figure 1:
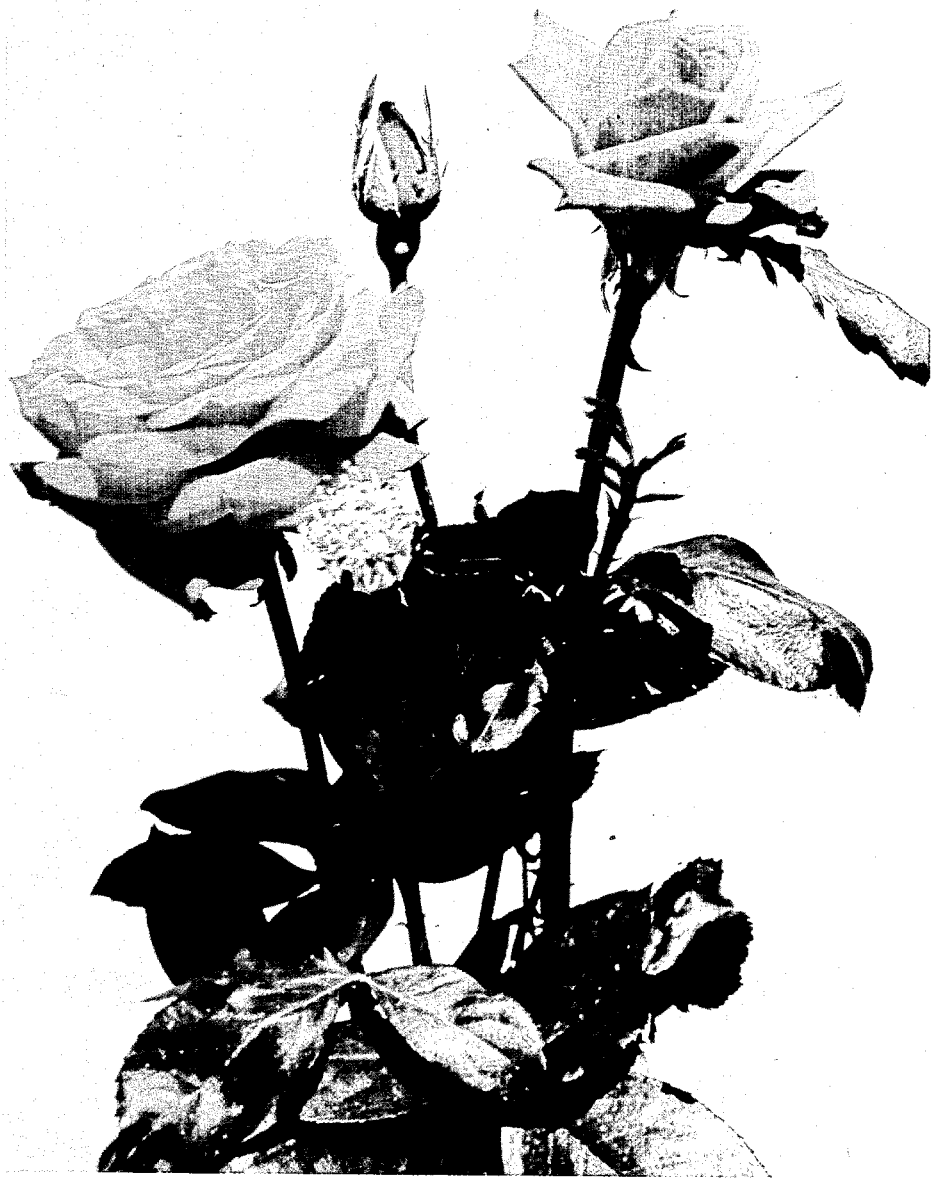
FIG. 1 is a view of a fully open bloom and a half open bloom, which show the shape and leaf characteristics, but is not intended to show the true color.
Figure 2:
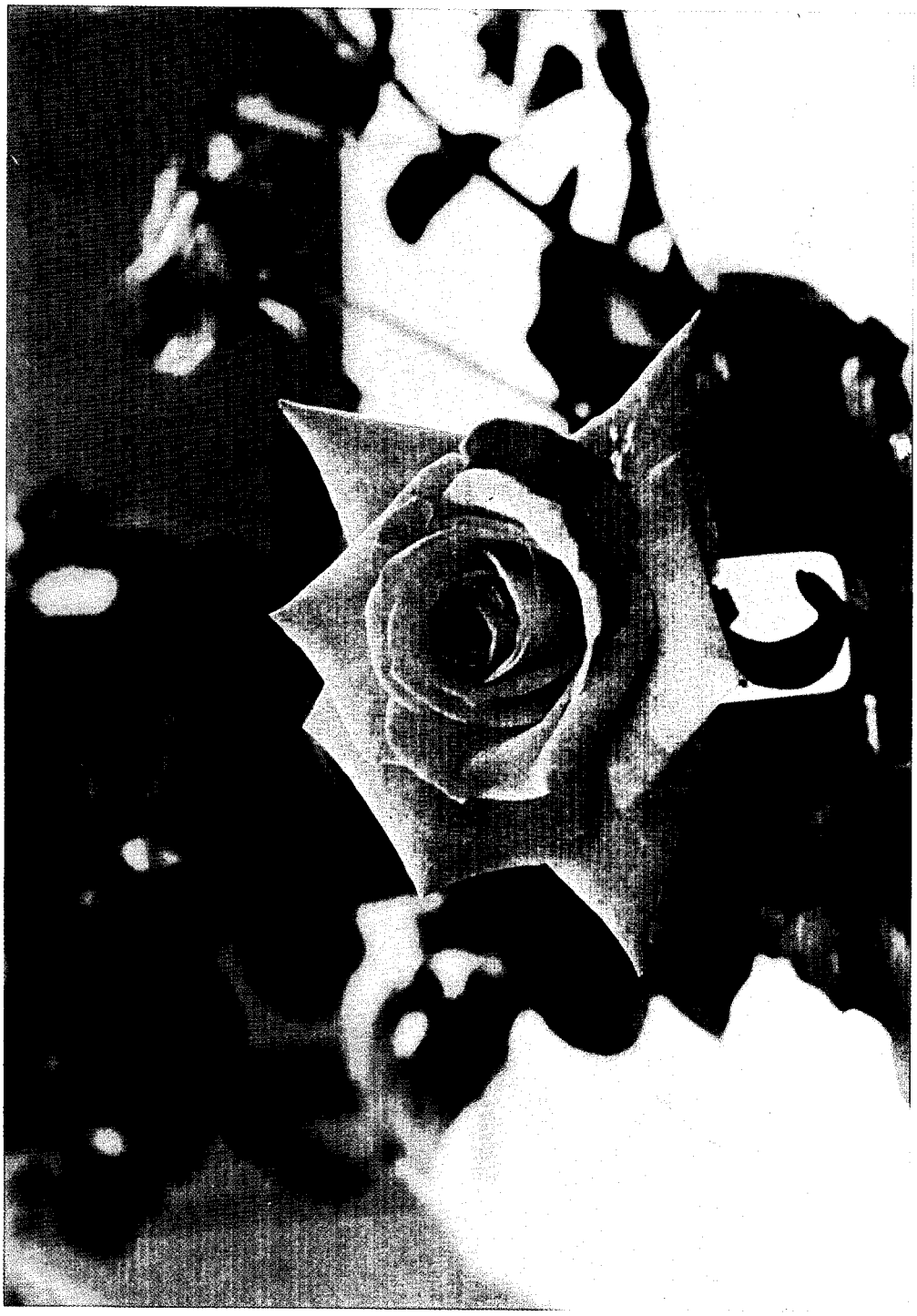
FIG. 2 is a view of an open bloom with side buds which more nearly shows the true color.

The following is a detailed description of my new variety in which the terminology of the colors corresponds to that of the Horticultural Color Chart of the Royal Horticultural Society, London, England.

Type: Hardy; bush; greenhouse and outdoor; sport; for cut flowers and garden decorations.
Class: Hybrid tea.
Propagation: It does hold its distinguishing characteristics through succeeding propagations by budding.

*Flower*

Locality where grown: Santa Ana, Calif.
Flowers Borne: Singly on a stem; on normal long stems.
Quantity of Bloom: Free, in greenhouse.
Continuity: Continuous.
Fragrance: Slight tea.
Bud: Peduncle: Long; medium; erect; medium green; smooth; few prickles; yellow green.
*Before calyx breaks.*—Size—medium. Form—medium ovoid with a conspicuous neck; with foliaceous appendages on the surface of the bud; with slender medium cut foliaceous parts extending beyond the tip of the bud equal to ¼ of its length.
*As calyx breaks.*—Color—Greyed-Purple Group 187B.
*As first petal opens.*—Size—medium; form—medium ovoid; color—outside—Red Group 53B; inside—Red Group 45B; opening—it does open up well. It is not affected by weather conditions as its parent may be.
Bloom:
*Size when fully open.*—Medium, 3¼ inches to 3½ inches.
*Petalage.*—Double; from 42 to 52 petals; arranged regularly.
*Form.*—Cupped full at first; becoming flat; petals remaining at first tightly cupped; outer petals becoming later at maturity loosely rolled outward while the center petals hold their bud shape.
Petals: Thick leathery; with inside satiny; outside satiny.
*Shape.*—Outer round; wtih base flat; with 1 notch; intermediate—round; apex with 1 tooth; inner—ovate; with 1 notch.

This description of a newly opened flower was made from a rose grown in a greenhouse in July 1970, at Santa Ana, Calif.
Color:
*Outer petal.*—Outside surface—Red Group 46A; inside surface—between 42A and 43A Red Group.
*Intermediate petal.*—Outside surface—Red-Purple Group 57A; inside surface—Red Group 43A.
*Inner petal.*—Outside surface—Red-Purple Group 57A; inside surface—Red Group 43A.

This description was made from a rose that was open for three days, indoors, in July 1970, at Santa Ana, Calif.
Color:
*Outer petal.*—Outside surface—Red Group 45A; inside surface—Red Group 44A.
*Inner petal.*—Outside surface—Red-Purple Group 57A; inside surface—Red Group 45C.
General color effect:
*Newly opened flower.*—Red Group 43A.
*Three days open.*—Red Group 43B.
Behavior: Petals persist; fading brown; effected by adverse weather conditions less than its parent.
Flower longevity: Cut roses grown in greenhouse kept at living room temperatures 7 to 8 days in July.

*Reproductive organs*

Stamens: Many; arranged regularly about pistils.
Filaments: Many; most with anthers; medium length. Color: Red Group 57B.
Anthers: All open at once; medium size. Seldom an anther fused with a petaloid or a pistil.
Pollen: Moderate; yellow.
Pistils: Many.
Styles: Uneven; medium length; medium heavy; bunched.
Stigma: Yellow.
Ovaries: Some protuding from receptacle.
Hips: None observed.
Sepals: Permanent; moderately long; recurved.
Seeds: None observed.

*Plant*

Foliage:

*Leaves.*—5; normal; medium to moderately large size; heavy. Moderately glossy somewhat less glossy than its parent.

*Leaflets.*—Shape: Oval with apex obtuse, base obtuse, margin simply dentate.

*Color.*—Mature — upper surface — Green Group 136B; under surface — Greyed - Green 194A; young — upper surface — Greyed-Purple 183A; under surface—Greyed-Red Group 182B.

*Rachis.*—Medium size; upper side—grooved; under side—Sparsely prickly.

*Stipules.*—Short to medium length; medium wide; with medium points; more than 45°.

*Disease.*—Resistance comparable to the average variety growing under the same cultural conditions.

Growth:

*Habit.*—Bushy, upright, much branched.

*Growth.*—Free, vigorous.

*Canes.*—Medium.

*Main stems.*—Bright. Color—Green Group 137B. *Prickles*—several Color.—Close to 195A with a purple tone. *Hairs.*—None.

*Branches.*—Bright. Color—Green Group 137B. *Prickles.*—Several. Color—close to 195A with a purple tone. *Hairs.*—None.

*New Shoots.*—Dull. Color.152B Yellow-Green Group with a purple tone. *Prickles*—Several. Color—Greyed-Red Group 179A. *Hairs.*—None.

Using the Horticultural Color Chart of the Royal Horticultural Society to describe a newly open flower of my new rose, grown at Santa Ana, Calif., the inside petal surface is Orient Red, Plate 819, with the outside petal surface Cardinal Red, Plate 822. These colors are consistent from outer petals to inner petals. A flower open three days in a greenhouse had a color difference so slight as not to be distinguishable. The general color effect of my rose is a richer, more vivid red when compared to its parent or to U.S. Plant Patent No. 2,545. The general color effect of my rose has less brown tone than its parent and has less blue than the rose in U.S. Plant Patent No. 2,545. My new rose has commercial potential, as shown by its more red color than U.S. Plant Patent No. 1,367 or U.S. Plant Patent No. 2,545 and because it has a bud of better and more uniform shape, giving a higher percentage of saleable blooms with unsaleable flowers seldom exceeding 5% while its parent will often have unsalenable flowers in excess of 20%, and the same is true of the rose in U.S. Plant Patent No. 2,545.

My new rose has somewhat fewer prickles than its parent. When compared to U.S. Plant Patent No. 2,545, my new rose has fewer prickles which are also much less prominent. This is a significant and desirable characteristic which serves to distinguish my new rose from U.S. Plant Patent No. 2,545 and which contributes to its acceptance by the trade and in the marketplace.

I claim:

1. A new and distinct variety of rose plant of the hybrid tea class substantially as herein shown and described, characterized particularly as to novelty by being generally similar to its parent variety Baccara (U.S. Plant Patent No. 1,367), but being essentially distinguished therefrom by having less yellow in the flower coloration therefore giving a truer red flower color which holds through all the life of the flower and through all seasons and is less affected by adverse weather conditions than its parent and whose color is more regular throughout the bloom from inner to outer petals, whose bud form and shape are more uniform giving a higher yield of good quality flowers which are produced in greater quantity because of stronger growth and more freely branched growth habit of the plant than its parent variety, with less glossy foliage than its parent and with other plant characteristics substantially the same as its parent.

No references cited.

ROBERT E. BAGWILL, Primary Examiner